(12) United States Patent
Lopez et al.

(10) Patent No.: US 8,515,779 B2
(45) Date of Patent: Aug. 20, 2013

(54) SYSTEMS AND METHODS FOR NATIONAL REGISTRY DATA COLLECTION AS PATIENT CARE IS CONDUCTED

(75) Inventors: John Lopez, Hinsdale, IL (US); Michelle Fennessy, Sacramento, CA (US); Susan J. Zelisko, Frankfort, IL (US); Corey Sartain, Clerendon Hills, IL (US)

(73) Assignee: Loyola University of Chicago, Maywood, IL (US)

( * ) Notice: Subject to any disclaimer, the term of this patent is extended or adjusted under 35 U.S.C. 154(b) by 0 days.

(21) Appl. No.: 13/535,157

(22) Filed: Jun. 27, 2012

(65) Prior Publication Data
US 2012/0330682 A1 Dec. 27, 2012

Related U.S. Application Data

(60) Provisional application No. 61/501,388, filed on Jun. 27, 2011.

(51) Int. Cl.
*G06Q 10/00* (2012.01)
*G06Q 50/00* (2012.01)

(52) U.S. Cl.
USPC .................................. 705/2; 705/3

(58) Field of Classification Search
USPC ........................................ 705/2–4
See application file for complete search history.

(56) References Cited

U.S. PATENT DOCUMENTS

| | | | |
|---|---|---|---|
| 6,283,761 B1 * | 9/2001 | Joao | 434/236 |
| 6,551,243 B2 | 4/2003 | Bocionek et al. | |
| 6,801,227 B2 | 10/2004 | Bocionek et al. | |
| 7,437,302 B2 | 10/2008 | Haskell et al. | |
| 7,742,931 B2 | 6/2010 | McElwain | |
| 7,788,111 B2 | 8/2010 | Haskell et al. | |
| 7,908,155 B2 * | 3/2011 | Fuerst et al. | 705/3 |
| 2001/0049610 A1 * | 12/2001 | Hazumi | 705/3 |
| 2003/0130872 A1 * | 7/2003 | Dvorak et al. | 705/2 |
| 2004/0032426 A1 | 2/2004 | Rutledge et al. | |
| 2004/0088192 A1 * | 5/2004 | Schmidt et al. | 705/3 |
| 2005/0177396 A1 | 8/2005 | Gottlieb et al. | |
| 2006/0004745 A1 | 1/2006 | Kuhn et al. | |
| 2006/0229911 A1 * | 10/2006 | Gropper et al. | 705/2 |
| 2007/0027715 A1 * | 2/2007 | Gropper et al. | 705/2 |
| 2007/0055545 A1 | 3/2007 | Maughan et al. | |
| 2007/0192140 A1 * | 8/2007 | Gropper | 705/3 |
| 2007/0226175 A1 | 9/2007 | Resnic et al. | |
| 2008/0027752 A1 * | 1/2008 | Phan et al. | 705/2 |

(Continued)

*Primary Examiner* — Robert Morgan
*Assistant Examiner* — Michael Tomaszewski
(74) *Attorney, Agent, or Firm* — John R. Kasha; Kelly L. Kasha; Kasha Law LLC

(57) ABSTRACT

A user interface is provided that requests clinical note data from a healthcare provider as a patient is being seen by the healthcare provider. The clinical note data requested includes data needed to populate one or more variables of one or more national registries and data needed to populate a clinical note medical record of an existing electronic medical records system. The clinical note data entered by the healthcare provider for the patient is received from the user interface. Automatically and at substantially the same time, the entered clinical note data needed to populate a clinical note medical record of an existing EMR system for the patient is stored in the existing EMR system, and the entered clinical note data needed to populate one or more variables for the patient for the one or more national registries is stored in a database.

20 Claims, 5 Drawing Sheets

(56) References Cited

U.S. PATENT DOCUMENTS

| | | |
|---|---|---|
| 2008/0052127 A1* | 2/2008 | Rosenfeld et al. ................ 705/3 |
| 2008/0154642 A1 | 6/2008 | Marble et al. |
| 2009/0089095 A1 | 4/2009 | Esham et al. |
| 2009/0177493 A1* | 7/2009 | Narayan ........................... 705/3 |
| 2010/0076786 A1 | 3/2010 | Dalton et al. |
| 2010/0174558 A1 | 7/2010 | Smith et al. |
| 2011/0166883 A1 | 7/2011 | Palmer et al. |
| 2011/0270632 A1* | 11/2011 | Manning et al. ................ 705/3 |

* cited by examiner

SYSTEMS AND METHODS FOR NATIONAL REGISTRY DATA COLLECTION AS PATIENT CARE IS CONDUCTED

CROSS-REFERENCE TO RELATED APPLICATION

This application claims the benefit of U.S. Provisional Patent Application No. 61/501,388 filed Jun. 27, 2011, which is incorporated by reference in its entirety.

INTRODUCTION

Collected patient information or data related to a specific disease, treatment, or healthcare discipline is called a disease or patient registry. Disease or patient registries that include data from multiple institutions or locations across the United States are referred to as national registries.

One exemplary collection of national registries is the national cardiovascular data registry (NCDR®). The NCDR® includes, for example, a number of hospital-based cardiovascular registries, a registry created in collaboration with The Society of Thoracic Surgeons, and a practice-based cardiovascular quality improvement registry. The hospital-based cardiovascular registries of the NCDR® include, for example, the ACTION Registry® for acute coronary syndrome patients, the CARE Registry® for revascularization and endarterectomy procedures, the CathPCI Registry® for diagnostic cardiac catheterization and percutaneous coronary interventions, the ICD Registry™ for implantable cardioverter defibrillators and leads, and the IMPACT Registry® for improving pediatric and adult congenital treatment.

Although the registries of the NCDR® are illustrative of national registries in general, the systems and methods described herein are not limited to the registries of the NCDR®. The systems or methods described herein can be used with any national registry for any disease, treatment, or healthcare discipline.

Providing data to national registries is encouraged and in some cases required by insurance companies and the federal government. For example, in some instances the federal government provides a higher reimbursement rate for a subsidized procedure, if the data from the procedure is sent to a national registry. In other instances, such as with medical devices, the federal government mandates that information about a certain medical device be tracked in a national registry. National registry data is also available in some instances, for public review by the Centers for Medicare and Medicaid Services (CMS) and allows for comparisons across hospital systems.

National registry data is useful to researchers and clinicians, because it includes a minimum number of values for a common set of data items for each patient. National registries are an important and unique source of a large body of retrospective, unselected consecutive patient data for researchers and research entities/institutes. Clinicians use the information in national registries to develop standards of care and to identify areas of practice improvement. Public review of national registry data to compare hospital systems on quality measures is increasingly available, highlighting the importance of accurate reporting for hospital systems to allow fair representation of the results of patient care. As a result, it is important that the data provided to national registries is accurate.

Public health agencies also require this information to monitor for adverse events associated with different therapies. Seamless reporting of this information allows providers and policy makers to know faster, act quicker, and develop solutions when adverse events occur Unfortunately, current methods of collecting and submitting data to national registries contribute to errors in the national registry data that can significantly reduce its accuracy. These errors are related to who collects the data, how it is collected, and when it is collected.

For example, national registry data is typically collected following an auditing procedure that begins after a patient is treated. A healthcare provider, such as a hospital, hires data entry personnel to gather national registry data from the medical records of patients. The medical records of patients can include, but are not limited to, test results, a patient's medical history, past treatments, insurance information, billing information, current course of treatment including orders, images, analyses, and healthcare provider reports. Medical record can be stored as charts or electronic medical records (EMR). Generally, national registry data consists of a minimum number of values for a common set of data items for a disease, treatment, procedure, or healthcare discipline that must be entered or a common set of questions that must be answered for each patient entered. The data entry personnel enter the data items or answer the questions based on the information they find in medical records of patients.

This current auditing approach to gathering national registry data can produce inaccurate results. First, data entry personnel, including clinicians, can incorrectly interpret the data from the medical records. In many cases, there is not a one-to-one correspondence between the information found in the medical records and the set of common data items required by the national registry. This leaves interpretation up to the personnel entering the data, who may not have provider level medical training.

Secondly, data entry personnel can manually enter incorrect data. Generally, data is copied by hand from the medical records to a file or database that is then uploaded to a national registry. Copying data by hand can include, but is not limited to, writing information on a paper form that is digitally read or entering data using a digital device such as a computer.

Thirdly, since the data is collected after a patient has been treated and the medical record completed, the medical records may not include enough or particular information to accurately enter a data item or answer a question needed by the national registry. The data charted in the process of patient care may not clearly provide the specific answers to the data items requested or required for national registry submission. Since at the time of national registry data collection the patient is no longer receiving care, any incomplete information has to be pieced together from existing information, entered by default, or left incomplete.

In addition to producing inaccurate results, this current auditing approach to gathering national registry data is expensive in terms of both time and cost. Currently, hospital systems have providers create data via the medical record as part of the clinical workflow, and much of this data is separately and redundantly recorded for national registry documentation. For large national data registries, several of which a hospital system may contribute to, it would be common for a hospital system to duplicate this data for thousands of patients in each registry annually. For example, data items that are common to a national registry and a medical record are entered into two different systems at two different times, thereby increasing the total data entry time. Since these data items are therefore collected by at least two different sets of personnel at different times, this increases the total cost of data entry, and often commands a significant time commitment from clinical providers, taking time away from patient care. It has been estimated by an NCDR survey that for every 800 records entered into a national registry, a participating hospital needs to hire an additional 1.0 full time equivalent (FTE).

Therefore, it is desirable to provide systems and methods that collect national registry data more accurately, faster, and less expensively than convention systems and methods, that incorporate this collection into the existing clinical workflow in a time and costs efficient manner.

BRIEF DESCRIPTION OF THE DRAWINGS

The skilled artisan will understand that the drawings, described below, are for illustration purposes only. The drawings are not intended to limit the scope of the present teachings in any way.

Figure 1:
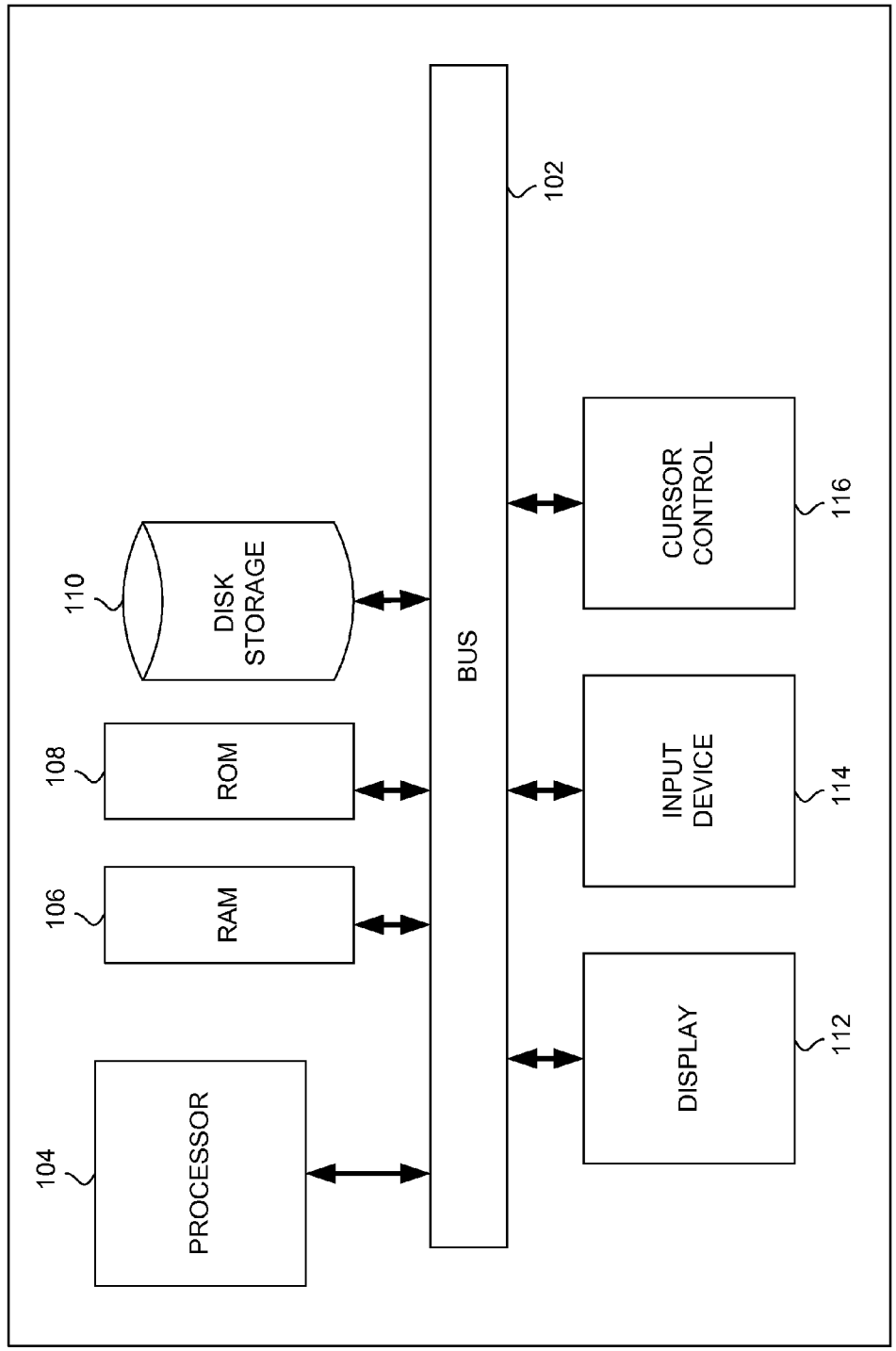
FIG. 1 is a block diagram that illustrates a computer system, in accordance with various embodiments.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

In various embodiments, computer system 100 can be connected to one or more other computer systems, like computer system 100, across a network to form a networked system. The network can include a private network or a public network such as the Internet. In the networked system one or more computer systems can store and serve the data to other computer systems. The one or more computer systems that store and serve the data can be referred to as servers or the cloud, in a cloud computing scenario. The other computer systems that send and receive data to and from the servers or the cloud can be referred to as client or cloud devices, for example.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Collecting National Registry Data

As described above, the conventional auditing approach to collecting national registry data often produces inaccurate results and is expensive in terms of both time and cost.

In various embodiments, systems and methods are provided that collect national registry data in conjunction with an existing electronic health records (EHR) or electronic medical records (EMR) system as patient care is conducted. Collecting national registry data as patient care is conducted produces more accurate results and reduces both the time and cost of data entry. More accurate results are produced because medically trained healthcare providers enter the data in the course of providing a medical record. Both the time and cost of data entry is reduced, because the data is entered only once by one group of personnel.

Collecting national registry data in conjunction with an existing EMR system is nontrivial, because national registries and existing EMR systems were developed for different purposes. EMR systems were developed for providing patient care and billing. National registries were developed for providing data on diseases, medical devices, or procedures and their outcomes across a large number of patients. As a result, national registries and EMR systems do not generally include the same data.

For example, an EMR system typically includes medication list. From the medication list of an EMR system it may be determined that a patient is taking aspirin. However, a particular national registry may have a data item that asks if aspirin was administered within 24 hours of a certain procedure. In addition, another national registry may have a data item that asks if aspirin was administered within seven days of a certain procedure. Consequently, the information in the EMR system that the patient is taking aspirin is not useful to either of the two national registries that ask about the administration of aspirin in relation to a procedure.

Therefore, in various embodiments collecting national registry data in conjunction with an existing EMR system includes a mapping of registry data to EMR system data. This mapping can include a number of steps, for example. In the first step, the set of data items per patient needed for one or more national registries is defined. A typical national registry can include 500 or more data items per patient, for example.

In the second step, data items from the set of data items per patient needed for the one or more registries are mapped to locations in the EMR system where similar data is collected as patient care is conducted. For example, if the set of data items per patient needed for two registries includes asking two questions about the timing of aspirin administration before a procedure, then these two questions are mapped to a medication list of an EMR system. In other words, a mapping is the logical union of distinct data items in the one or more registries and the EMR system.

In the third step, locations in the EMR system that are mapped to data items from the set of data items per patient needed for the one or more registries are modified. For example, the medication list of an existing EMR is modified to include the questions described above relating a time of the administration of aspirin to a procedure. Note that locations in the existing EMR are modified by modifying a user interface of an existing EMR system, for example. The user interface is modified by editing a template, flowsheet, or user interface form of the existing EMR system, for example.

In various embodiments, an existing EMR system cannot be modified. In this case, a user interface is developed for a system outside of the existing EMR system. This is, for example, a meta user interface. This meta user interface includes all of the data items of the existing EMR system plus additional data items or fields needed for the national registry data.

Alternatively, a companion application/user interface is developed. A companion application and user interface, for example, monitors the clinical note data being supplied to the user interface of the existing EMR system. Monitoring can include, but is not limited to, monitoring input device input, such as keystrokes, or running the entire user interface of the existing EMR system inside the companion application and user interface. When the companion application/user interface determines that data being entered is similar to the data required for a national registry, the companion application/user interface prompts the healthcare provider for that information.

For example, a companion application and user interface can determine that a healthcare provider has entered the word "aspirin." The companion application and user interface can then prompt the healthcare provider with a question asking if aspirin was administered 24 hours before a procedure is scheduled.

Once the set of data items for one or more national registries are defined, data items are mapped to locations of an existing EMR system, and the mapped locations of the existing EMR system are modified, the existing EMR system automatically collects data for the one or more national registries as patient care is being conducted.

In various embodiments, collecting national registry data as patient care is being conducted includes acquiring information as soon as a patient enters a healthcare facility, such as a hospital, and continues throughout the clinical workflow until a patients exits the facility. Upon entering a healthcare facility, for example, the first data recorded in an EMR system is typically a history and physical (H&P). An H&P is, for example, a clinical observation, note, or document created by a healthcare provider. A healthcare provider can include, but is not limited to, a physician, physician assistant, or advanced practice nurse. Throughout a patient's contact with a healthcare facility additional clinical notes are collected in the EMR. These clinical notes may be added to the H&P, or may be stored as separate documents in the EMR, for example.

Clinical note data includes, but is not limited to, H&P, past treatments, insurance information, billing information, current course of treatment including orders, procedure notes, outcome information, complications, or discharge orders. Hereinafter the H&P or any clinical note entered by a healthcare provider at any time during an encounter with a patient at a healthcare facility is referred to as a clinical note.

In various embodiments, a user interface is provided to healthcare provider for collecting national registry and clinical note information together. This user interface is, for example, a template, a flowsheet, or a user interface form. The same template, flowsheet, or user interface form includes both existing EMR system data items and national registry data items, so that the final destination of the data collected is unknown to the healthcare provider requesting the information.

Note that this user interface is different from conventional third-party software that is used to collect national registry data. Generally this conventional third-party software also includes a user interface for collecting national registry data. However, this conventional third-party software is typically not integrated with existing EMR system. In addition, the user interface of the conventional third-party software for collecting national registry data does not include both existing EMR system data items and national registry data items tightly integrated on the same template, flowsheet, or user interface form.

Also, conventional third-party software templates are built to manage only one registry at a time. So for example, if a hospital uses one third-party software vendor for registry collection, they are able to collect data for one registry (CathPCI Registry® for cardiac catheterization procedure) but they are unable to collect for patients who present for a heart attack (ACTION Registry®). In addition, a patient may present and ultimately be submitted for three or more registries that are associated for a single hospital admission. For example, a patient with a heart attack (ACTION Registry® data needed) undergoes cardiac catheterization (CathPCI Registry® data needed), undergoes surgery (STS/ACC TVT Registry™), and requires post-surgery pacemaker/defibrillator (ICD Registry™ data). Therefore, one patient can be submitted to four different registries from a single hospitalization. Since there is a lack of integration within conventional third-party software vendors, hospitals are required to manually collect for all four registries.

In various embodiments, a user interface for collecting national registry and clinical note information together includes predetermined data items for entering data specific to a national registry. For example, predetermined data items can include, but are not limited to, pulldown menus, selection lists, or radio buttons populated with a finite set of data choices for each national registry data item. Predetermined items can increase the accuracy of the data entered by preventing incorrect or incomplete information from being entered.

In various embodiments, a user interface for collecting national registry and clinical note information together also generates data for a national registry and clinical note or document for an existing EMR system at substantially the same time. Essentially, the data entered and collected together is now parsed and stored separately by the user interface.

After collecting national registry and clinical note information together using a user interface, data collection continues throughout the clinical workflow until a patient exits the facility. This data collection can include, but is not limited to, pulling or pushing data from other parts of an existing EMR system or from other systems of the health care facility. The additional clinical workflow data can include, but is not limited to, test results, procedure reports or notes, post-procedure documentation, and discharge information including complications at the time of discharge. The additional data can be pulled or pushed at the time it is available or at periodic data reconciliation times in batch mode, for example.

In various embodiments, national registry data generated by a user interface or received from other parts of an existing EMR system or from other systems of the health care facility is stored in a separate database. Once enough data is collected to populate the minimum data items required for a national registry for one or more patients, this data is automatically uploaded to the national registry. This data can be uploaded in any format required by the national registry. An exemplary format for uploading national registry data is extensible markup language (XML).

In various embodiments, national registry data generated by a user interface or received from other parts of an existing EMR system or from other systems of the health care facility is validated before being uploaded to a national registry. Validation of the national registry data can include any combination of automatic and manual validation. Automatic validation can include, but is not limited to, verifying that a minimum number of data items are populated, or verifying that the data entered for two or more data items are consistent. In addition, a healthcare provider can be notified if a minimum number of data items are populated or if two or more data items are consistent by running a validation report, for example.

Manual validation can include, but is not limited to, providing a validation user interface. A healthcare provider can use the validation user interface to review national registry data before it is submitted, for example.

National Registry Data Collection System

Figure 2:
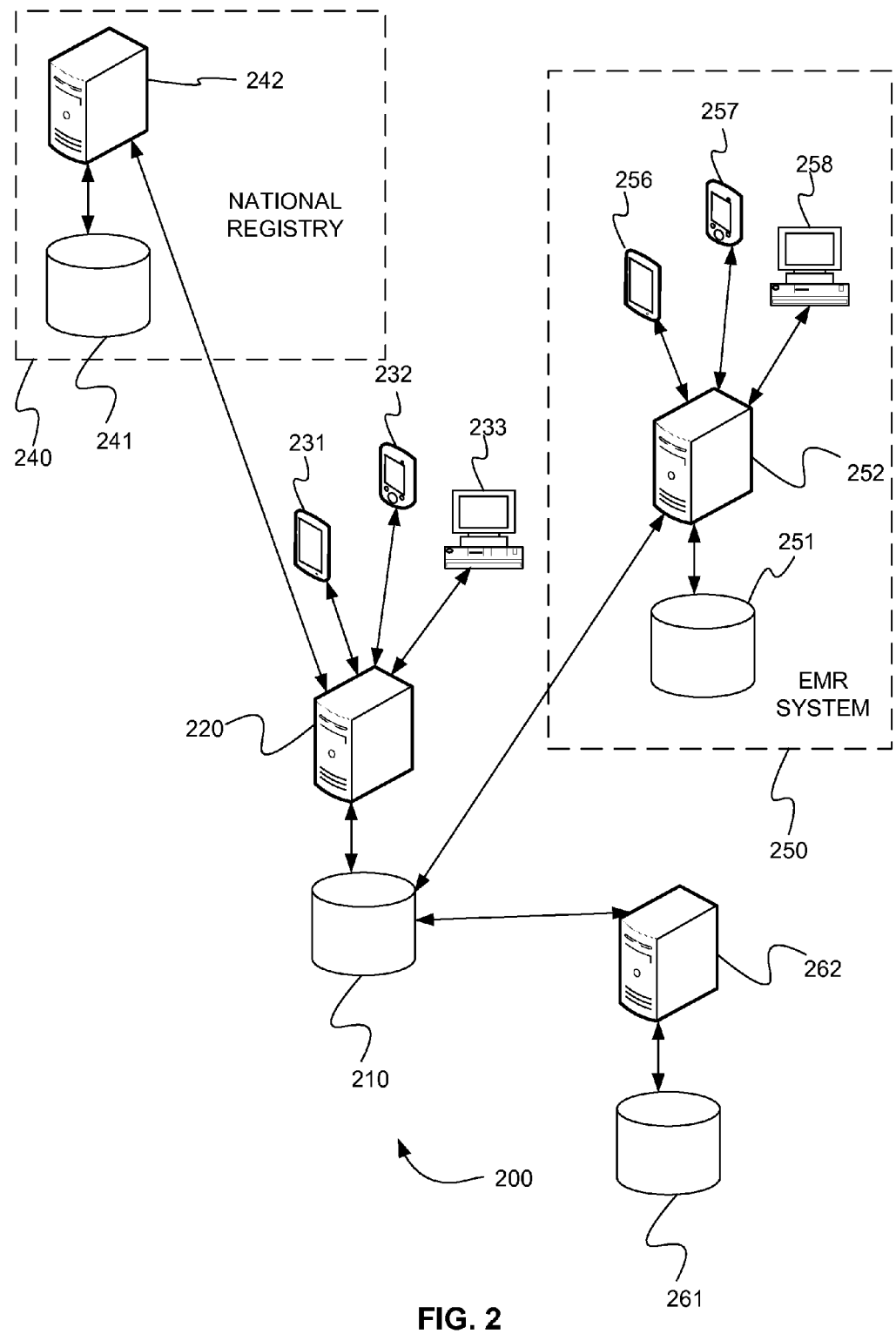
FIG. 2 is a schematic diagram showing a system for collecting national registry data in conjunction with an existing electronic medical records system as patient care is conducted, in accordance with various embodiments.

FIG. 2 is a schematic diagram showing a system 200 for collecting national registry data in conjunction with an existing EMR system as patient care is conducted, in accordance with various embodiments. System 200 includes database 210 and processor 220. Database 210 includes any type of magnetic or electronic storage. Database 210 can be part of the storage for processor 220 or it can be storage that is external to processor 220. Database 210 can include its own processor or can be entirely controlled by processor 220. Database 210 can be part of the cloud in a cloud computing environment, for example.

Database 210 stores a plurality of variables per patient for submission to one or more national registries. For example, database 210 stores a plurality of variables per patient for submission to national registry 240. National registry 240 can include a database 241 for storing national registry data and a processor 242 for receiving data from healthcare providers. Database 210 can include a software database program running on a processor of database 210 or a software database program running on processor 220.

Processor 220 is in communication with the database 210. Processor 220 can be connected directly to database 210 or can be connected to database 210 across one or more networks. Processor 220 can be any type of computer system, such as the computer system of FIG. 1.

Processor 220 provides a user interface that requests clinical note data from a healthcare provider as a patient is being seen by the healthcare provider. Processor 220 can directly display a user interface on a display or processor 220 can be part of a client/server system that displays the user interface. For example, processor 220 can be a server in a client/server system that includes one or more client devices. Client devices can include, but are not limited to, a tablet computing device 231, a smartphone, music player, or personal digital assistant 232, or a client computer 233.

In various embodiments, processor 220 can be the processor of tablet computing device 231, smartphone, music player, or personal digital assistant 232, or client computer 233. In other words, tablet computing device 231, smartphone, music player, or personal digital assistant 232, or client computer 233 can be connected directly to database 210.

Clinical note data includes, for example, clinical observations, demographic information, and lists of medications. The clinical note data requested includes data needed to populate one or more variables of one or more national registries and data needed to populate a clinical note medical record of an existing EMR system. The clinical note data requested includes data needed to populate one or more variables of national registry 240 and data needed to populate a clinical note medical record of EMR system 250, for example.

EMR system 250 can include a database 251 for storing a clinical note medical record and a processor 252 for receiving data from healthcare providers. Like processor 220, processor 252 can directly display a user interface on a display or processor 252 can be part of a client/server system that displays the user interface. For example, processor 252 can be a server in a client/server system that includes one or more client devices. Client devices can include, but are not limited to, a tablet computing device 256, a smartphone, music player, or personal digital assistant 257 or a client computer 258.

Processor 220 receives the clinical note data entered by the healthcare provider for the patient from the user interface. The user interface may be displayed on tablet computing device 231, smartphone, music player, or personal digital assistant 232, or client computer 233, for example. The user interface can be a template, a flowsheet, or a user interface form, for example.

Finally, automatically and at substantially the same time, processor 220 stores portions of the clinical note data in the existing EMR system and database 210 for the patient. Processor 220 stores the entered clinical note data for a clinical note medical record in the existing EMR system for the patient. For example, processor 220 stores data for a clinical note medical record in EMR system 250. Processor 220 sends this information to processor 252 of EMR system 250 for storage in database 251, for example.

At substantially the same time, processor 220 stores the entered clinical note data needed to populate one or more variables for the patient for the one or more national registries in database 210. Processor 220 stores the entered clinical note data needed to populate one or more variables for the patient for national registry 240, for example. One skilled in the art can appreciate that the phrase "substantially the same time" can include exactly at the same time and also at times that differ by only a few seconds.

Processor 220 stores portions of the clinical note data in existing EMR system 250 and database 210 for the patient after a single click of a submit or file button on the user interface, for example. Upon receiving the single click of the submit button, processor 220 segregates the data and stores the segregated data in existing EMR system 250 and database 210. Segregation of the data and storage of the data are automatic and require no direction from the healthcare provider. The segregated data is not, for example, sent to existing EMR system 250 and then moved from EMR system 250 to database 210 or a national registry, as is performed by some conventional third-party software.

In various embodiments, a second processor is in communication with database 210. The second processor can be processor 252 of EMR system 250. The second processor retrieves data from the existing EMR for the patient over time and stores the retrieved data in database 210 in order to complete population of a minimum number of variables for the patient for one or more national registries. The one or more national registries include national registry 240, for example.

The second processor 252 of EMR system 250 pulls data from database 251 and pushes it to database 210 as shown in FIG. 2, for example. One skilled in the art can appreciate, however, that any combination of processor 220 and processor 252 can be used to move data from database 251 to database 210 over time.

In various embodiments, the second processor retrieves data from the existing EMR system for the patient during an entire hospitalization. For example, second processor 252 of EMR system 250 pulls data from database 251 and pushes it to database 210 during an entire hospitalization, for example. Again, one skilled in the art can appreciate, that any combination of processor 220 and processor 252 can be used to move data from database 251 to database 210 during an entire hospitalization of the patient.

In various embodiments, the second processor can be a processor of any system of a healthcare facility. For example, the second processor can be a processor of system for storing test results or procedure documentation. Processor 262 is an exemplary processor of system of a healthcare facility other than EMR system 250. The second processor can be processor 262 and can pull data from database 261, for example.

In various embodiments, processor 220 validates the populated minimum number of variables stored in database 210 for the patient. Certain data points must be present in order to submit cases. Therefore, missing data from these particular variables will prevent submission of a case. System 200 can notify a healthcare provide that these data points are required to submit the case after he/she runs a validation report, for example.

In various embodiments, processor 220 validates the populated minimum number of variables stored in database 210 for the patient by comparing the timing of the entered clinical note data stored in the database for the patient and the data retrieved over time for the patient from the existing EMR system.

In various embodiments, processor 220 exports the validated populated minimum number of variables stored in database 210 for a patient to one or more national registries. The one or more national registries include national registry 240, for example. Processor 220 uploads the validated populated minimum number of variables stored in database 210 for a patient to national registry 240 using XML, for example.

In various embodiments, processor 220 removes patient identifying information from the validated populated minimum number of variables stored in database 210 for the patient before exporting the validated populated minimum number of variables stored in database 210 for the patient to the one or more national registries.

In various embodiments, processor 220 automatically exports the validated populated minimum number of variables stored in database 210 for the patient to the one or more national registries when the populated minimum number of variables stored in the database is validated.

In various embodiments, processor 220 exports the validated populated minimum number of variables stored in database 210 for the patient to the one or more national registries after the validated populated minimum number of variables are reviewed by a healthcare provider. For example, processor 220 provides a user interface that a healthcare provider uses to review data stored in database 210 before it is uploaded.

In various embodiments, the user interface provided by processor 220 of reviewing national registry data includes a select/deselect feature. Using this feature, cases may be removed from submission. For example, a case that is not a true heart attack case can be removed from the national registry data by deselecting the case for submission. Processor 220 records the deselected case in database 210 along with the name of the healthcare provider who removed the case and the date/time, so there is transparency in the data submission process. This select/deselect feature can help prevent hospitals from selecting only the best cases for submission to a national registry. There is a discussion in the healthcare community about the potential for hospitals to "cherry pick" cases to help improve their outcome reports. Deselected cases are not submitted, but these data can be audited, so as to ensure that hospitals are transparent in their data submission process.

In various embodiments, clinical note data requested by user interface is found by comparing clinical note data needed to populate variables of the one or more national registries and clinical note data needed to populate a medical record of an existing EMR system. The clinical note data requested by the user interface is the logical union of the clinical note data needed to populate variables of the one or more national registries and clinical note data needed to populate a medical record of an existing EMR system, for example.

In various embodiments, the data requested to populate one or more variables of the one or more national registries and the data requested to populate a clinical note medical record of an existing EMR system appear on the same form in the user interface. In contrast to third party software for submitting national registry data, various embodiments do not separate national registry data and data requested to populate a clinical note medical record in the user interface.

In various embodiments, processor 220 stores the entered clinical note data in the existing EMR system for the patient by generating a clinical note data document from the entered clinical note data and storing the clinical note data document in the existing EMR system. For example, the user interface provided by processor 220 generates a clinical note data document from the entered clinical note data and stores the clinical note data document in database 251 of EMR system 250.

In various embodiments, processor 220 is processor 252 of EMR system 250. In other words, processor 252 is modified to perform the functions of processor 220 as described above. As a result, the user interface for entering data may be displayed on tablet computing device 256, smartphone, music player, or personal digital assistant 257, or client computer 258, for example. Processor 252 is modified or programmed to perform the functions of processor 220 by editing a template, flowsheet, or user interface form displayed by processor 252, for example.

In various embodiments, however, it is not possible to modify or program processor 252 to perform the functions of processor 220 as described above. As a result, processor 220 is not part of EMR system 250. In addition, processor provides a meta user interface to collect the same information as the user interface produced by processor 252 of EMR system 250 plus the information needed for the national registry.

National Registry Data Collection Method

Figure 3:
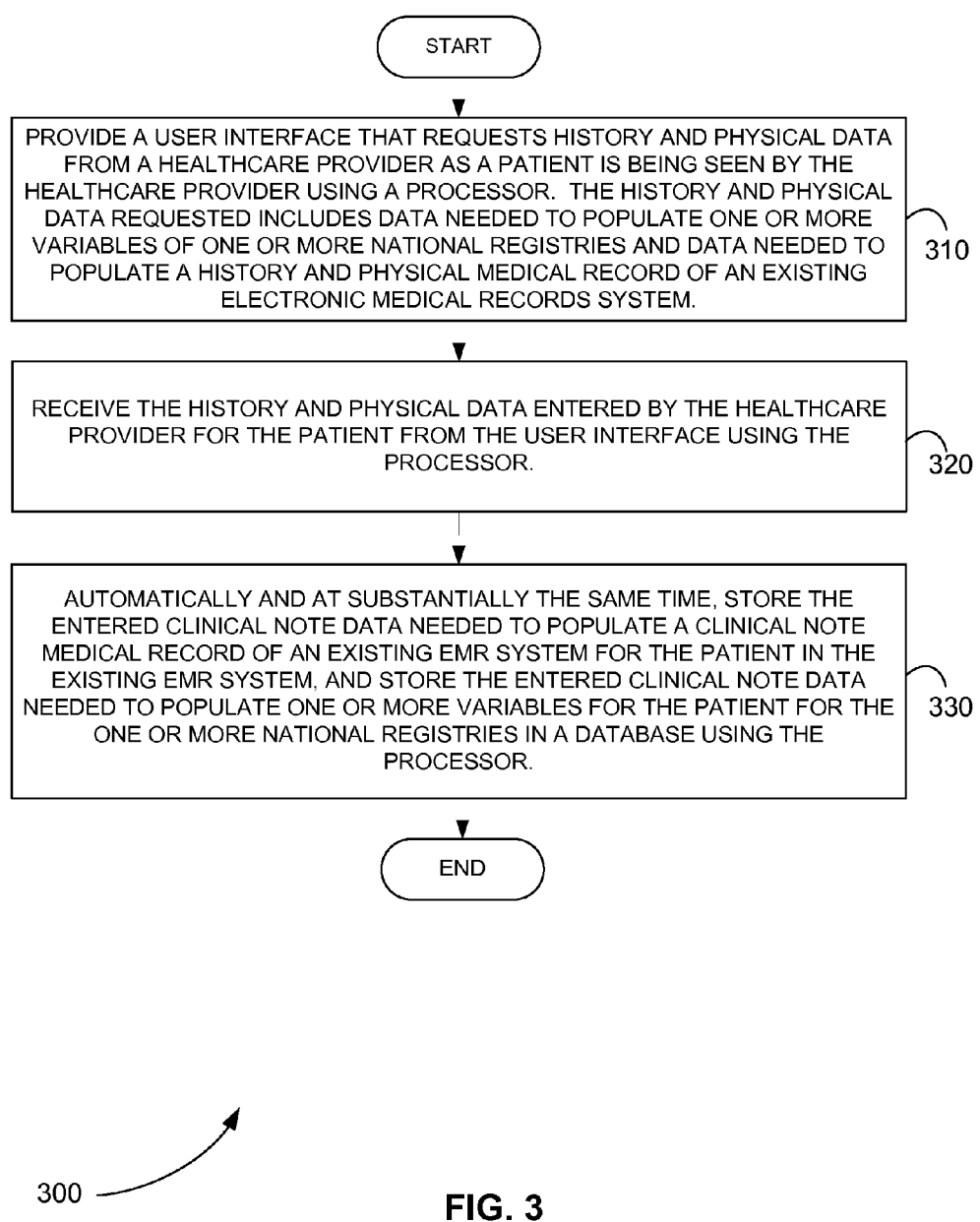
FIG. 3 is an exemplary flowchart showing a method for collecting national registry data in conjunction with an existing electronic medical records system as patient care is conducted, in accordance with various embodiments.

FIG. 3 is an exemplary flowchart showing a method 300 for collecting national registry data in conjunction with an existing EMR system as patient care is conducted, in accordance with various embodiments.

In step 310 of method 300, a user interface is provided that requests clinical note data from a healthcare provider as a patient is being seen by the healthcare provider using a processor. The clinical note data requested includes data needed to populate one or more variables of one or more national registries and data needed to populate a clinical note medical record of an existing EMR system.

In step 320, the clinical note data entered by the healthcare provider for the patient is received from the user interface using the processor.

In step 330, automatically and at substantially the same time, the entered clinical note data needed to populate a clinical note medical record of an existing EMR system for the patient is stored in the existing EMR system, and the entered clinical note data needed to populate one or more variables for the patient for the one or more national registries is stored in a database using the processor. The database stores a plurality of variables per patient for the one or more national registries.

National Registry Data Collection Computer Program Product

In various embodiments, a computer program product includes a non-transitory and tangible computer-readable storage medium whose contents include a program with instructions being executed on a processor so as to perform a method for collecting national registry data in conjunction with an existing EMR system as patient care is conducted. This method is performed by a system that includes one or more distinct software modules.

Figure 4:
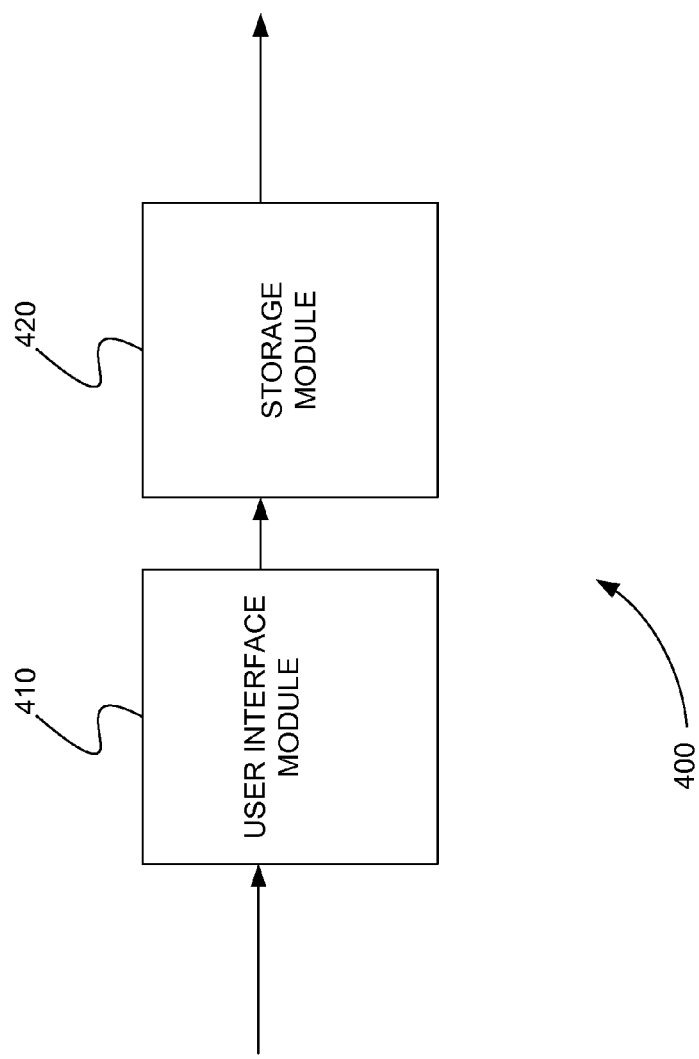
FIG. 4 is a schematic diagram of a system that includes one or more distinct software modules that perform a method for collecting national registry data in conjunction with an existing electronic medical records system as patient care is conducted, in accordance with various embodiments.

FIG. 4 is a schematic diagram of a system 400 that includes one or more distinct software modules that perform a method for collecting national registry data in conjunction with an existing EMR system as patient care is conducted, in accordance with various embodiments. System 400 includes user interface module 410 and storage module 420;

User interface module 410 provides a user interface that requests clinical note data from a healthcare provider as a patient is being seen by the healthcare provider. The clinical note data requested includes data needed to populate one or more variables of one or more national registries and data needed to populate a clinical note medical record of an existing EMR system. User interface module 410 receives clinical note data entered by the healthcare provider for the patient from the user interface.

Storage module 420 automatically and at substantially the same time, stores the entered clinical note data needed to populate a clinical note medical record of an existing EMR system for the patient in the existing EMR system, and stores the entered clinical note data needed to populate one or more variables for the patient for the one or more national registries in a database. The database stores a plurality of variables per patient for the one or more national registries using the storage module.

Data Example

Figure 5:
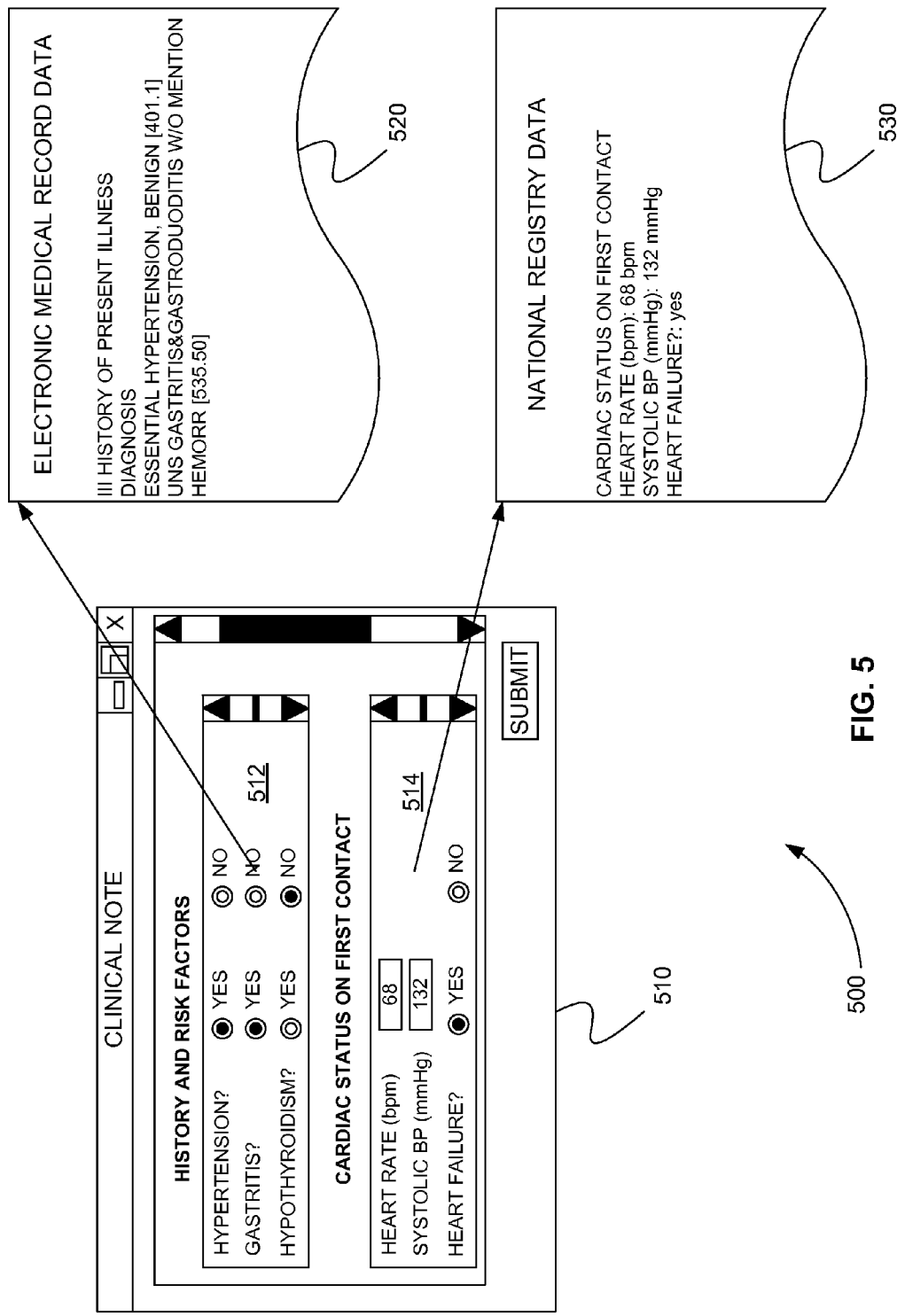
FIG. 5 is a data example showing how electronic medical record data and national registry data is automatically and at substantially the same time submitted to two different databases, according to various embodiments.

FIG. 5 is a data example 500 showing how electronic medical record data and national registry data is automatically and at substantially the same time submitted to two different databases, according to various embodiments. User interface 510 includes, on the same form, fields 512 for entering clinical note data for an existing EMR system, and fields 514 for entering for national registry data for one or more national registries. User interface 510 can be, but is not limited to a form, template, or flowsheet. It is not apparent to a user that the data entered using user interface 510 is segregated and sent to two different databases upon submission.

As shown in FIG. 5, data is segregated into electronic medical record data and national registry data, and the segregated data is stored in database 520 of an existing EMR system and database 530 that stores data for submission to one or more national registries. The data is automatically segregated and sent by user interface 510 after a user clicks on the submit button, for example.

Essentially, user interface 510 simultaneously creates a required clinical note and a template or file for data uploading to one or more national registries, for example. The required clinical note is stored in database 520 of an existing EMR system and the template or file for data uploading is stored in database 530, for example. Thus, the creation of clinically relevant documentation is part of the national registry data collection process that is integrated into the normal clinical workflow.

In FIG. 5, the data is shown as being segregated into two types of data and each type of data is sent to one database. In various embodiments, an existing EMR can benefit by including one or more items of the national registry data. As a result, one or more items from the national registry data can be sent to both database 520 and database 530, for example.

In addition and in various embodiments, the questions asked for an existing EMR system and a national registry may overlap. As a result, data entered in user interface 510 can be sent to both database 520 and database 530, for example.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for collecting national registry data in conjunction with an existing electronic medical records system as patient care is conducted, comprising:
a database that stores a plurality of variables per patient for one or more national registries; and
a processor in communication with the database that
in order to simultaneously collect data required to populate one or more variables of one or more national registries and data needed to populate a clinical note medical record of an existing electronic medical records system as a patient is being seen by a healthcare provider, provides a user interface that requests clinical note data from the healthcare provider and displays on the user interface at the same time both the data required to populate one or more variables of the one or more national registries and the data needed to populate a clinical note medical record of an existing electronic medical records system,
receives the clinical note data entered by the healthcare provider for the patient from the user interface,
determines that the clinical note data being entered is similar to the data required to populate one or more variables of the one or more national registries and prompts the healthcare provider to enter the data required to populate one or more variables of the one or more national registries, and
automatically and at the same time stores the entered clinical note data needed to populate a clinical note medical record in the existing electronic medical records system for the patient and stores the entered clinical note data required to populate one or more variables for the patient for the one or more national registries in the database.

2. The system of claim 1, further comprising a second processor in communication with the database that retrieves data from the existing electronic medical records for the patient over time and stores the retrieved data in the database in order to complete population of a minimum number of variables for the patient for the one or more national registries.

3. The system of claim 2, wherein the second processor that retrieves data from the existing electronic medical records for the patient during an entire hospitalization.

4. The system of claim 1, wherein the processor validates the populated minimum number of variables stored in the database for the patient.

5. The system of claim 4, wherein the processor validates the populated minimum number of variables stored in the database for the patient by comparing the timing of the entered clinical note data stored in the database for the patient and the data retrieved over time for the patient from the existing electronic medical records system.

6. The system of claim 4, wherein the processor exports the validated populated minimum number of variables stored in the database for the patient to the one or more national registries.

7. The system of claim 6, wherein the processor removes patient identifying information from the validated populated minimum number of variables stored in the database for the patient before exporting the validated populated minimum number of variables stored in the database for the patient to the one or more national registries.

8. The system of claim 6, wherein the processor automatically exports the validated populated minimum number of variables stored in the database for the patient to the one or more national registries when the populated minimum number of variables stored in the database is validated.

9. The system of claim 6, wherein the processor exports the validated populated minimum number of variables stored in the database for the patient to the one or more national registries after the validated populated minimum number of variables are reviewed by a healthcare provider.

10. The system of claim 1, wherein clinical note data requested by the user interface is found by comparing clinical note data required to populate variables of the one or more national registries and clinical note data needed to populate a medical record of an existing electronic medical records system.

11. The system of claim 1, wherein the data requested to populate one or more variables of the one or more national registries and the data requested to populate a clinical note medical record of an existing electronic medical records system appear on the same form in the user interface.

12. The system of claim 1, wherein the processor stores the entered clinical note data in the existing electronic medical records system for the patient by generating a clinical note data document from the entered clinical note data and storing the clinical note data document in the existing electronic medical records system.

13. The system of claim 1, wherein the processor comprises a client device.

14. The system of claim 1, wherein the processor comprises a server computer.

15. The system of claim 1, wherein the processor comprises a processor of the existing electronic medical records system.

16. The system of claim 1, wherein the processor comprises a processor not part of the existing electronic medical records system.

17. The system of claim 2, wherein the processor and the second processor are the same device.

18. The system of claim 2, wherein the processor and the second processor are different devices.

19. A method for collecting national registry data in conjunction with an existing electronic medical records system as patient care is conducted, comprising:
   in order to simultaneously collect data required to populate one or more variables of one or more national registries and data needed to populate a clinical note medical record of an existing electronic medical records system as a patient is being seen by a healthcare provider, providing a user interface that requests clinical note data from the healthcare provider and displaying on the user interface at the same time both the data required to populate one or more variables of one or more national registries and the data needed to populate a clinical note medical record of an existing electronic medical records system using a processor;
   receiving the clinical note data entered by the healthcare provider for the patient from the user interface using the processor;
   determining that the clinical note data being entered is similar to the data required to populate one or more variables of the one or more national registries and prompting the healthcare provider to enter the data required to populate one or more variables of the one or more national registries; and
   automatically and at the same time, storing the entered clinical note data needed to populate a clinical note medical record in the existing electronic medical records system for the patient and storing the entered clinical note data required to populate one or more variables for the patient for the one or more national registries in the database using the processor.

20. A computer program product, comprising a non-transitory and tangible computer-readable storage medium whose contents include a program with instructions being executed on a processor so as to perform a method for collecting national registry data in conjunction with an existing electronic medical records system as patient care is conducted, the method comprising:
   providing a system, wherein the system comprises one or more distinct software modules, and wherein the distinct software modules comprise a user interface module and a storage module;
   in order to simultaneously collect data required to populate one or more variables of one or more national registries and data needed to populate a clinical note medical record of an existing electronic medical records system as a patient is being seen by a healthcare provider, providing a user interface that requests clinical note data from the healthcare provider and displaying on the user interface at the same time both the data required to populate one or more variables of one or more national registries and the data needed to populate a clinical note medical record of an existing electronic medical records system;
   receiving the clinical note data entered by the healthcare provider for the patient from the user interface using the user interface module;
   determining that the clinical note data being entered is similar to the data required to populate one or more variables of the one or more national registries and prompting the healthcare provider to enter the data required to populate one or more variables of the one or more national registries; and
   automatically and at the same time, storing the entered clinical note data needed to populate a clinical note medical record in the existing electronic medical records system for the patient and storing the entered clinical note data required to populate one or more variables for the patient for the one or more national registries in the database using the storage module.

* * * * *